US00PP10545P

United States Patent [19]

Bjorge et al.

[11] Patent Number: Plant 10,545

[45] Date of Patent: Aug. 11, 1998

[54] 'FA 47' PEACH TREE

[75] Inventors: Annette Bjorge; Randy Bjorge, both of Coloma, Mich.

[73] Assignee: International Plant Management, Lawrence, Mich.

[21] Appl. No.: 738,257

[22] Filed: Oct. 28, 1996

[51] Int. Cl.[6] ..... A01H 5/00

[52] U.S. Cl. ..... Plt./43.1

[58] Field of Search ..... Plt./43.1

*Primary Examiner*—James R. Feyrer

[57] ABSTRACT

A new peach variety, *Prunus persica*, (hereinafter referred to as the 'FA 47' peach tree) which was developed by Annette and Randy Bjorge in a breeding program at Fruit Acres Farm in Coloma, Mich., having the following combination of unique and desirable features:

1. A fruit with excellent shipping and storage qualities.
2. A fruit maturing 7 days before the 'Redhaven' peach.
3. A substantially round fruit with clear yellow flesh and an attractive orange-red stripe coloration covering 75% of the fruit at maturity.
4. A fruit with flesh that does not brown when it is cut.
5. A tree and fruit with good resistance to Bacterial Spot.
6. A tree and blossom that is very hardy.

3 Drawing Sheets

ORIGIN OF THE VARIETY

The new variety of peach tree 'FA 47' was developed by Annette and Randy Bjorge in a peach breeding program at Fruit Acres Farms, 2559 Friday Road, Coloma, Mich., 49038. The FA 47 peach tree was developed as a first generation cross between 'Newhaven' and 'Jim Dandee' (U.S. Plant Pat. No. 5,223, two established commercial varieties. The parent tree was grown and maintained in a peach tree breeding orchard on Fruit Acres Farms.

This new and distinct variety of peach tree has been asexually propagated by budding at Fruit Acres Farms in Coloma, Mich. The asexual propagation demonstrates that such reproduction of the characteristics of the tree are consistent and are established and transmitted through succeeding generations.

SUMMARY OF THE VARIETY

The new and distinct variety of peach tree is of weeping growth with medium density and is regular and productive bearer of peaches. The fruit of the new variety is characterized by round, substantially 75% blushed red fruits on the mostly exposed surfaces which suffuses to a indistinct red on red stripe over a bright yellow background on the less exposed surfaces. The fruits have firm flesh and are resilient to the extent that they may be handled and packaged mechanically without damaging the same for shipment. This results in less spoilage and a greater market value. The flesh of the fruits of the new variety does not brown when cut. The fruits of the new variety have a recessed pistil point which avoids damage during picking and handling. The tree and fruits of the new variety exhibit good resistance to Bacterial Spot and are very cold hardy. The fruit matures at the beginning of the peach growing season in Southwestern Michigan. It ripens 7 days before the established commercial variety, 'Redhaven'.

BRIEF DESCRIPTION OF THE PHOTOGRAPHS

The accompanying photographs show typical specimens of the new variety in color as nearly true as it is reasonably possible to make the same in color illustrations of this character. The specimens were photographed in Van Buren and Berrien counties of Southwestern Michigan.

Figure 1:
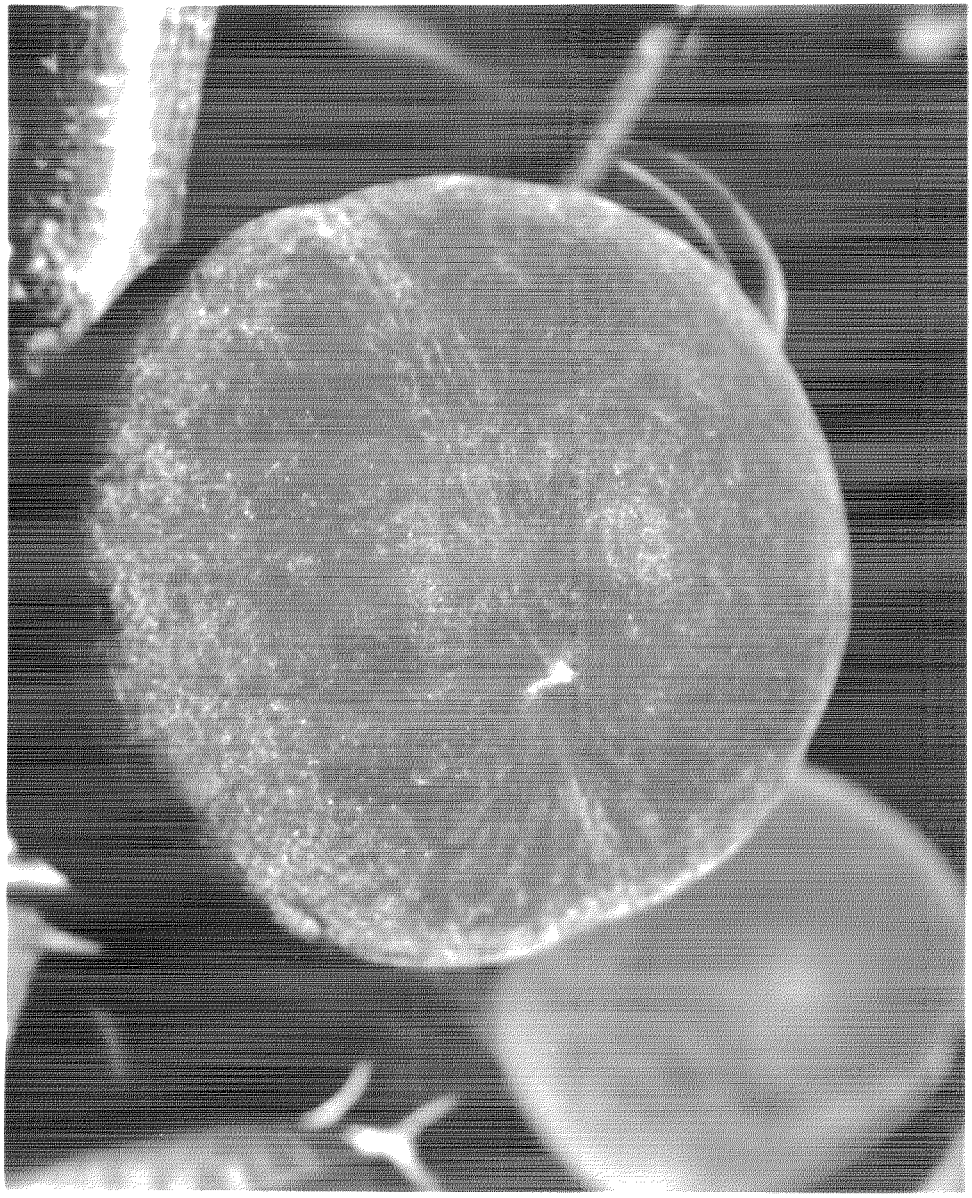
FIG. 1 illustrates specimens of the fully ripened fruit and foliage of the new variety.
Figure 2:
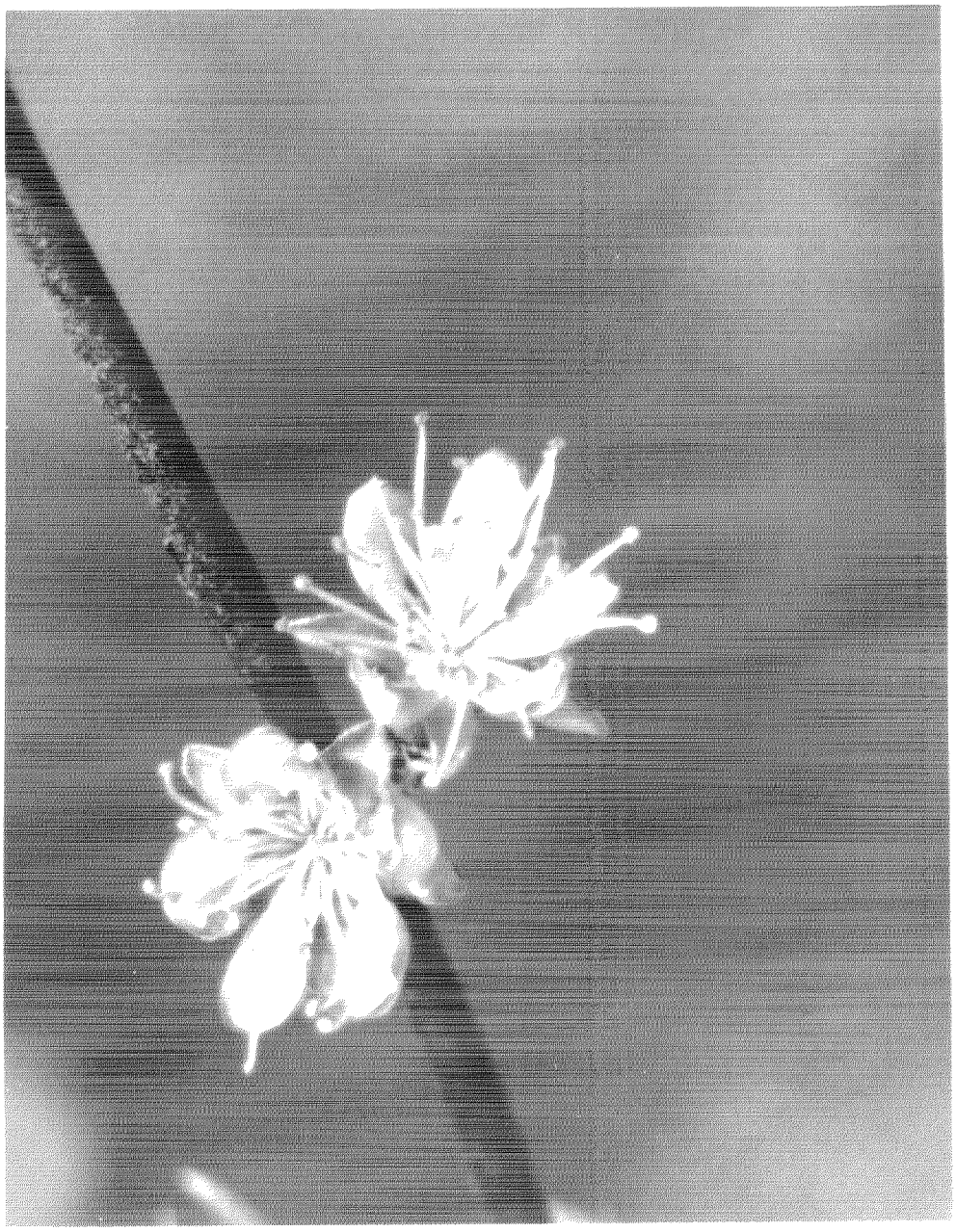
FIG. 2 illustrates blooms of the new variety.
Figure 3:
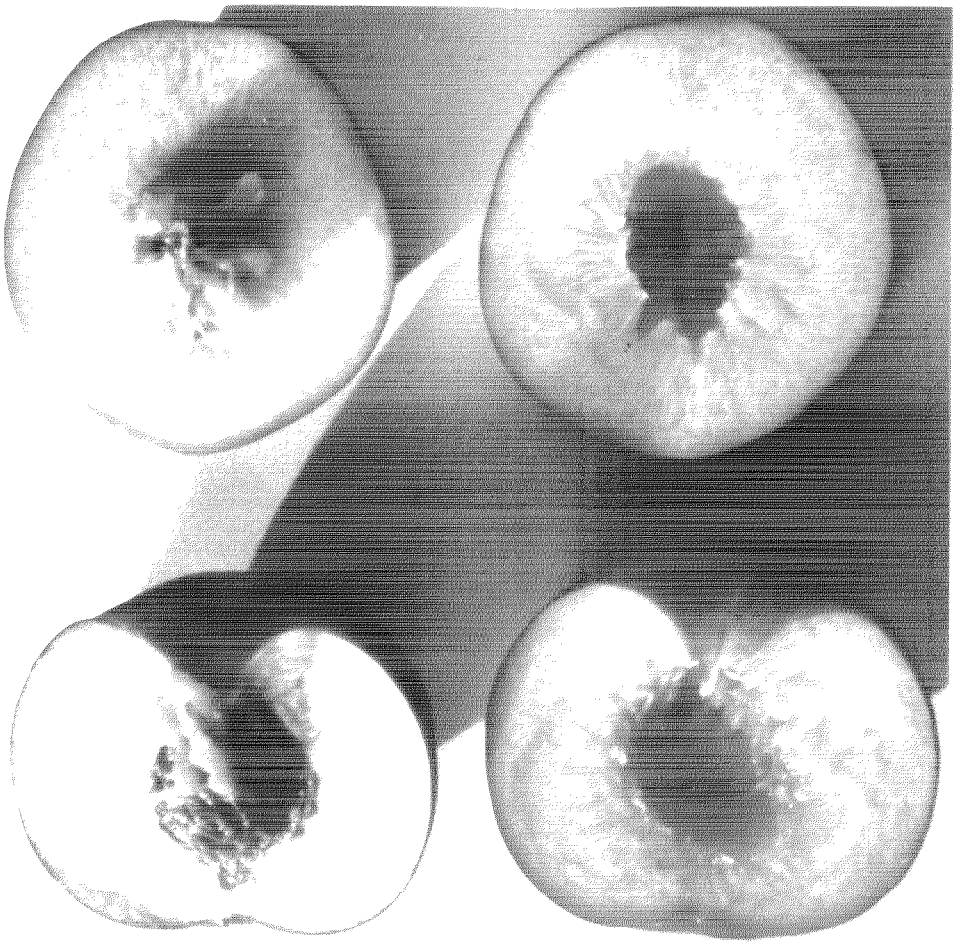

FIG. 3 Illustrates two specimens of the new variety. The lower specimen is bisected along the suture, the upper specimen is bisected as a ninety-degree angle to the plane of the suture. The color and forms of the flesh, pit and pit cavity are illustrated.

DETAILED DESCRIPTION OF THE VARIETY

The following description of the fruit and foliage of the new variety is based on observations of specimens grown in Berrien and Van Buren County of southwestern Michigan. The color terminology is in accordance with The Royal Horticultural Society Colour Chart, published by The Royal Horticultural Society of London, England.

Tree:

*Age of specimen.*—15 years
*Height.*—4.3M.
*Width.*—4.3M.
*Size.*—Medium.
*Vigor.*—Vigorous, requires spring pruning and must be thinned early and diligently to obtain good fruit size.
*Density.*—Open, internode length averages 1 to 1½ cm.
*Form.*—Low, weeping, major scaffold branches form a 50° to 60° angle to the trunk, tree forms a central leader and does not need supplement support.
*Production.*—Similar to 'Redhaven', not as productive as 'Jim Dandee', more productive than 'Newhaven', ripens in 3 pickings with 20% of the crop ready for the first picking, and 40% respectively for the second and third pickings. Harvest season lasts 7 days in a normal years. Fruits will hold 10 days on the tree.
*Bearing.*—Annual.
*Disease resistance.*—Good resistance to bacterial spot.
*Cold hardiness.*—Very hardy, hardier than 'Redhaven' and 'Jim Dandee' parents.

Trunk:

*Size.*—Small.
*Surface.*—Smooth.
*Lenticils.*—Medium.
*Color.*—Gray 201 A.

Leaves:

*Size.*—Length 155 mm, width 36 mm.

*Form.*—Lanceolate, pointed.

*Thickness.*—Medium.

*Texture.*—Medium.

*Margin.*—Serrate.

*Petiole.*—18 mm, medium, thickness.

*Glands.*—Round, number varies from 2 to 5, average 4. Located on the base of the leaf and upper portion of petiole.

*Color.*—Upper surface Green 147 A, lower surface Green 147 B.

*Stipules.*—None.

Flower buds:

*Size.*—Medium.

*Length.*—Medium.

Flowers:

*Blooming period.*—April 8 to 15 in Coloma, Mich.

*Presentation.*—Medium showy.

*Pollen.*—Present, self fertilizing.

*Petals.*—5 in number, cupped inward, length 9 mm, width 5 mm, Red-Purple 73 A.

*Stamens.*—Length 18 mm, White 155 A.

*Pistil.*—Lenghth — 17 mm, White 155 A.

Fruit:

*Maturity when described.*—Firm ripe.

*Date of first picking.*—July 26th in southwestern Michigan, 7 days before Redhaven.

*Size.*—60 mm to 75 mm.

*Form.*—Round.

*Suture.*—Very shallow, indistinct.

*Pistil point.*—Recessed.

Skin:

*Thickness.*—Thin to medium.

*Texture.*—Medium fine.

*Tendency to crack.*—Slight.

*Down.*—Slight.

*Color.*—Solid blush, Red 46 A which suffuses to an indistinct, mottled stripe Red 46 C over 70% of the surface, over a background of Yellow-Orange 20B.

Flesh:

*Texture.*—Fine.

*Aroma.*—Medium, pleasant, very distinctive.

*Fibres.*—Few, small, tender, not conspicuous or noticeable in eating.

*Color.*—Yellow-Orange 10 A, some Red 43 A in mid fruit.

*Eating quality.*—Best, with very good flavor for the early season, medium acid with good acid/sugar balance.

*Coloration at the pit.*—Flesh is clear yellow around virtually 100% of the pit cavity.

Stone:

*Size.*—Length 39 mm, width 25 mm, thickness 17 mm.

*Form.*—Ovate.

*Apex.*—Pointed.

*Sides.*—Nearly equal.

*Base.*—Straight.

*Surface.*—Pitted to furrowed throughout.

*Color.*—Grayed-orange 165 C.

*Type.*—Semi-freestone.

*Tendency to crack.*—None.

Use. Desert, fresh market and commercial.

Shipping quality. Excellent.

Keeping quality. Excellent, will hold for 3 weeks in common cold storage.

Disease resistance. Good resistance to bacterial spot and peach canker.

I claim:

1. A new and distinct variety of peach tree, *Prunus persica*, substantially as herein shown and described, characterized particularly as to novelty by the unique combination of vigorous, weeping, open, medium density, regular bearing tree, with resistance to bacterial spot, producing semi-freestone fruits having yellow, non-browning flesh and substantially round, firm, 95% striped orange-red skin color at maturity which occurs 7 days before 'Redhaven' peach.

* * * * *

FA 47